United States Patent [19]

Avidan et al.

[11] Patent Number: 4,873,385
[45] Date of Patent: Oct. 10, 1989

[54] SINGLE ZONE OLIGOMERIZATION OF LOWER OLEFINS TO DISTILLATE UNDER LOW SEVERITY IN A FLUID BED WITH TAILORED ACTIVITY

[75] Inventors: Amos A. Avidan, Yardley; David L. Johnson, Glen Mills, both of Pa.

[73] Assignee: Mobil Oil Corp., New York, N.Y.

[21] Appl. No.: 197,543

[22] Filed: May 23, 1988

Related U.S. Application Data

[63] Continuation-in-part of Ser. No. 6,407, Jan. 23, 1987, Pat. No. 4,746,762.

[51] Int. Cl.⁴ .............................................. C07C 2/12
[52] U.S. Cl. ..................................... 585/415; 585/533
[58] Field of Search ............................... 585/415, 533

[56] References Cited

U.S. PATENT DOCUMENTS

| | | | |
|---|---|---|---|
| 4,456,781 | 6/1984 | Marsh et al. | 585/533 |
| 4,504,693 | 3/1985 | Tabak et al. | 585/520 |
| 4,542,247 | 9/1985 | Chang et al. | 585/533 |
| 4,543,435 | 9/1985 | Gould et al. | 585/330 |
| 4,544,780 | 10/1985 | Daviduk et al. | 585/533 |
| 4,547,612 | 10/1985 | Tabak | 585/533 |
| 4,554,396 | 11/1985 | Chang et al. | 585/533 |
| 4,579,999 | 4/1986 | Gould et al. | 585/640 |
| 4,689,205 | 8/1987 | Gould et al. | 585/469 |
| 4,746,762 | 5/1988 | Avidan et al. | 585/533 |

FOREIGN PATENT DOCUMENTS 2156381 10/1985 United Kingdom ................. 585/533

*Primary Examiner*—Asok Pal
*Attorney, Agent, or Firm*—Alexander J. McKillop; Charles J. Speciale; Lowell G. Wise

[57] ABSTRACT

A turbulent, dense fluid-bed of a medium pore zeolite metal-losilicate catalyst, the bed having a tailored distribution of weight fractions of particles having activities which fall generally along a predetermined curve of activity distribution, is operated under low severity conditions at low WHSV, under moderate pressure and moderate severity to obtain surprisingly high conversion to $C_5+$ hydrocarbons having an olefin content in excess of about 80%, about one third by weight of which is distillate ($C_9+$). Only a small amount of cyclo-olefins and a negligibly small amount of aromatics and paraffins are produced. The distillate is formed with a single pass yield in the range from about 10-40 weight percent. The reactor is operated only in the distillate mode. The dense fluid bed has a density, measured at the bottom of the reaction zone, less than 640 kg/m³ (40 lb/ft³), and preferably operates at a temperature in the range from about 250° C. (482° F.) to about 371° C. (700° F.), and a pressure in the range from above about 200 kPa (15 psig) but below about 2800 kPa (400 psig). Despite operating under "easy" conditions, this unique process provides per pass conversion of olefins, and selectivity to $C_5+$ hydrocarbons, each in excess of 80%.

12 Claims, 2 Drawing Sheets

SINGLE ZONE OLIGOMERIZATION OF LOWER OLEFINS TO DISTILLATE UNDER LOW SEVERITY IN A FLUID BED WITH TAILORED ACTIVITY

CROSS-REFERENCES TO RELATED APPLICATIONS

This application is a continuation-in-part of U.S. Patent application Ser. No. 006,407 filed Jan. 23, 1987, now U.S. Pat. No.4,746,762.

BACKGROUND OF THE INVENTION

This invention relates to a fluid-bed catalytic process for upgrading olefinic light gas feedstock (termed "light gas" for brevity herein) containing lower, particularly $C_3$–$C_5$, olefins (alkenes) and paraffins (alkanes). The olefins are converted to distillate in a single-zone fluid-bed reactor, operating at moderate pressure and temperature, ("low severity" conditions). These operating conditions are referred to herein as "easy", and the process is referred to as a low severity MOD (for "Mobil Olefin to Distillate") process. By "distillate" we refer to $C_9$+ hydrocarbons boiling in the range from about 130° C. to about 300° C. (266° F. −572° F.) We know of no other process which can convert olefins with at least 80% conversion and about 20% by weight (wt %) single pass yield, to distillate, in a single zone.

More particularly, the invention provides a continuous process for oligomerizing light gas containing a $C_3$–$C_5$ olefin, namely propene, butenes and pentenes, a mixture thereof, or mixtures thereof with a minor proportion by weight of paraffins, preferably only $C_1$–$C_5$ paraffins, in the absence of added hydrogen, to a $C_9$+ rich hydrocarbon stream, in a highly efficient operating mode because of a fluid catalyst bed with "tailored" activity. By "$C_9$+rich" we refer to the presence of at least 10% by weight of $C_9$+ hydrocarbons in the product. By "tailored" activity we refer to a bed which consists essentially of weight fractions, in a specified range, of equilibrated low activity catalyst particles, the weight fraction in each range having a specified activity (alpha) in defined ranges below 10, and less than 10 wt % of the catalyst has an activity greater than 10.

The alpha value for catalyst activity is defined by the specific test described in U.S. Pat. Nos. 3,827,968 and 3,960,978 to Givens et al, the disclosures of which are incorporated by reference thereto as if fully set forth herein.

Developments in fluid-bed catalytic processes using a wide variety of zeolite catalysts have spurred interest in commercializing the conversion of olefinic feedstocks for producing $C_5$+ gasoline, diesel fuel, etc. In addition to the discovery that the intrinsic oligomerization reactions are promoted by ZSM-5 type zeolite catalysts, several discoveries relating to implementing the reactions in an apt reactor environment, have contributed to the commercial success of current industrial processes. These are environmentally acceptable processes for utilizing feedstocks that contain lower olefins, especially $C_3$–$C_5$ alkenes, though some ethene (ethylene), and some olefins and paraffins heavier than $C_5$ may also be present.

Of particular interest is that the ZSM-5 type catalyst used under our "easy" process conditions, and also as used under the severe process conditions of Ser. No. 006,407, does not appear to suffer from a sensitivity (poisoning) to basic nitrogen-containing organic compounds such as alkylamines (e.g. diethylamine), or, to oxygenated compounds such as ketones, a proclivity which is characteristic of the catalyst under the process conditions of prior art olefin oligomerization processes, particularly the fixed bed processes operated at very high pressure. Such processes require the addition of hydrogen as a preventitive antidote. It will be recognized that alkylamines are used in treating light gas streams, and ketones are typically present in Fischer Tropsch-derived light ends streams, both of which streams are particularly well-suited for upgrading by oligomerization. Though our process is not adversely affected by the presence of hydrogen, there is no readily discernible economic incentive for using it in our single stage reactor, and we prefer not to do so.

Prior art moderate pressure processes using a zeolite catalyst to oligomerize lower olefins under comparable temperature conditions produced excellent conversions to distillate range olefins in a fixed bed microreactor but neglected to state what the alpha value of their catalyst was; nor did they suggest that the alpha value might be of over-riding significance (see "Conversion of $C_2$–$C_{10}$ Olefins to Higher Olefins Over Synthetic Zeolite ZSM-5" by W. E. Garwood presented at the Symposium on Advances in Zeolite Chemistry before the Division of Petroleum Chemistry, Inc., American Chemical Society, Las Vegas Meeting Mar. 28–Apr. 2, 1962).

When the low severity process is carried out in a fluid bed using a relatively "high alpha" catalyst (above 100), the result is formation of a mixture of aromatics, naphthenes and paraffins, and a minor proportion by wt of olefins. Even when our process is carried out in a fluid bed with a relatively uniform low alpha in the range from 1 to 5, that is, none of the catalyst has an alpha greater than 5, niether the high conversion to $C_5$+ olefins, nor the high selectivity to $C_9$+ is obtained.

Conversion of $C_3$–$C_5$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the ZSM-5 type zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity; so do Dwyer et al in U.S. Pat. No. 3,700,724. Garwood et al have also contributed to the understanding of catalytic olefin upgrading techniques and have contributed improved processes as in U.S. Pat. Nos. 4,150,062, 4,211,640 and 4,227,992. The '062 patent discloses conversion of olefins to gasoline or distillate in the range from 190°–315° C. and 42–70 atm; and this, and the '640 and '992 disclosures are incorporated by reference thereto as if fully set forth herein.

The '978 patent discloses that low alpha ZSM-5 and ZSM-11 catalysts not only have reduced activity for cracking n-hexane and other paraffins, but also produce less than 10% by wt aromatics. The runs were made in a fixed bed microreactor, and, at that time, it was not known that the process was not operable on a larger scale without the addition of hydrogen to control coke deposition and to prevent poisoning of the catalyst by nitrogen-containing organic impurities. The basic knowledge that low activity ZSM-5 and ZSM-11 type catalysts effectively oligomerized lower olefins was used to arrive at improvements in "Conversion of LPG Hydrocarbons to Distillate Fuels or Lubes Using Integration of LPG Dehydrogenation and MOGDL" in U.S. Pat. No. 4,542,247 to Chang et al which discloses fixed beds in a two-stage catalytic process for converting olefins to gasoline and distillate; and, more recently, in "Catalytic Conversion of Olefins to Higher Hydrocarbons" in U.S. Pat. No. 4,456,779 to Owen et al. which discloses oligomerization of olefins in three down-flow fixed beds, in series, with intercoolers. Both fixed-bed processes require the addition of hydrogen for the reasons given hereinabove.

The low severity conditions under which our process produces distillate from lower olefins is particularly unexpected because it was generally accepted that relatively high severity was essential to obtain conversions of economic significance. Never has there been any suggestion that a tailored weight fraction distribution of equilibrated low activity catalyst particles might have a dominating effect on the oligomerization of a lower olefin feed if the process conditions were aptly chosen.

The prior art processes relate to the conversion of lower olefins, especially propene and butenes, over ZSM-5 and HZSM-5, at moderately elevated temperatures and pressures. The sought-after conversion products are liquid fuels, especially the $C_6+$ aliphatic and aromatic hydrocarbons. It is known that the product distribution may be tailored by controlling process conditions, such as temperature, pressure and space velocity. Gasoline ($C_6$-$C_{10}$) is readily formed at elevated temperature (preferably about 400° C.) and pressure from ambient to about 2900 kPa (420 psia), preferably about 250 to 1450 kPa (36 to 210 psia). Olefinic gasoline can be produced in good yield and may be recovered as a product or fed to a low severity, high pressure reactor system for further conversion to heavier distillate-range products. Distillate mode operation can be employed to maximize production of $C_9+$ aliphatics by reacting the lower and intermediate olefins at high pressure and moderate temperature. Operating details for typical "MOGD" (for Mobil Olefin to Gasoline & Distillate) oligomerization units are disclosed in U.S. Pat. Nos. 4,456,779 and 4,497,968 (Owen et al); 4,433,185 (Tabak); and U.S. Patent application Ser. No. 006,407.

We have now found that $C_3$-$C_4$-rich and higher olefins may be selectively upgraded to normally liquid hydrocarbons in the distillate range by catalytic conversion in a turbulent fluidized bed of solid acid ZSM-5 type of zeolite catalyst at least 90 wt % of which has an equilibrated alpha less than 10, and the remainder an alpha above 10, most preferably operating at a pressure below 1480 kPa (200 psig) in the dense phase, in the absence of added hydrogen, in a single pass, or with recycle of undesired oligomerized product.

Such operation results in the most important advantage of our MOD process, namely the use of a relatively low cost, low pressure reactor in which close temperature control is afforded by operation of a fluid-bed in the turbulent regime (referred to as a "turbulent bed"). An essentially uniform conversion temperature may be maintained (often with closer than +5° C. tolerance) to ensure that the distribution of activity of the catalyst weight fractions lies generally along a predetermined curve. Except for a small zone adjacent the bottom gas inlet, the midpoint measurement of conditions in the bed is representative of the entire bed, due to the thorough mixing achieved.

Moreover, in turbulent beds, fluidization is better at a higher fluidizing gas velocity, and with a higher level of the finer sizes of catalyst (see R. M. Braca and A. A. Fried, in *Fluidization,* D. F. Othmer, Ed. (Reinhold, New York, 1956), pp. 117–138; W. W. Kraft, W. Ulrich, W. O'Connor, ibid., pp. 184–211). This requires a significant amount of fines, from about 10 to 25% by weight (% by wt) having a particle size less than 32 microns. Since it is difficult to control the distribution and activity of catalyst fines it would seem at cross-purposes deliberately to require operation with a predetermined weight fraction of fines.

U.S. Pat. Nos. 4,417,086 and 4,417,087 to Miller teach a two-zone reactor operating in the transport mode where the relative superficial gas velocity is greater than the terminal velocity in free fall. There is no suggestion that the activity of the bed be tailored by specifying weight fractions of catalyst particles, all having relatively low equilibrated activity. Though the operation of a fluid-bed is illustrated (example 2 in each of the '086 and '087 patents) note that no operating pressure is stated in the former, and that operating pressure in the latter is 10 psig (24.7 psia, 170 kPa). The general disclosure that the processes may be operated at a pressure in the range from subatmospheric to several hundred atmospheres, but preferably 10 bar or less, and most preferably 0 to 6 bar, (see middle of col 6 in 086, and, near top of col 5 in '087) is not so ingenuous as to be meant to apply equally to the fixed bed (example 1 of '086 and '087, each illustrates 34.5 bar, 500 psi) and the 170 kPa fluidbed.

SUMMARY OF THE INVENTION

It has been discovered that a turbulent dense fluid-bed of a medium pore zeolite metallosilicate catalyst having a low equilibrated average activity (alpha) in the range from 1 to about 10 as a result of a particular distribution of alphas in preselected weight fractions of the bed which operates at low WHSV (it being understood that WHSV signifies pounds of feed per pound of zeolite per hour), under "easy" conditions of pressure and temperature, will nevertheless oligomerize a "light gas" feed containing $C_2$-$C_6$ olefins (predominantly $C_3$-$C_5$ olefins, the remainder being $C_3$-$C_5$ lower alkanes), to $C_9+$ distillate range hydrocarbons, a minor proportion of $C_9-$ aliphatic and naphthenic gasoline components, and essentially no aromatics. By "essentially no aromatics" we refer to a negligible amount, less than about 5%, typically less than 2% by wt, of the product.

In our MOD process, light gas containing a substantial, preferably a major portion, typically more than 75% of combined propene and butenes, is a particularly well-suited feed to the fluid-bed reactor. The presence of paraffins is not deleterious, but under the conditions of our process, they are left essentially unreacted and are therefore kept to a minimum in the feedstream. The conversion of ethylene, if present, is only about 50% at 315° C. (600° F.) and is therefore also kept to a minimum. The MOD reactor is operated at relatively low pressure in the range from about 200 kPa to about 2860 kPa (15 psig–400 psig), and moderate temperature in the range from 250° C. to about 371° C. (482° F.–700° F.) to produce a relatively large fraction (about 20% by wt, or more) of distillate which is at least 50% by wt olefins, in a single pass. A minor amount of $C_5+$, mainly $C_9-$, gasoline range hydrocarbons may also be formed. When such $C_5$-$C_9$ gasoline range olefins are formed, they are typically not a desired product in our process, and are therefore separated from the product. The separated olefins may be used as reactants to produce any of numerous products in known processes, or the olefins may be blended into gasoline, or, recycled in our process to yield desired distillate, or, reactive tertiary olefins are converted into ethers, or, lower and intermediate olefins may be reacted at high pressure and moderate temperature to form $C_{10}+$ aliphatics which are valuable products in an oil refinery.

More specifically, to produce desirable oligomerized product effectively, it has been discovered that when the dense phase fluid bed, referred to hereinabove, is operated at superatmospheric pressure, preferably above about 270 kPa (25 psig) but below 1480 kPa (200 psig) at a WHSV in the range from about 0.05 hr$^{-1}$ to about 5 hr$^{-1}$ with a catalyst fines content in the range from about 10% to 20%, the product contains more than 60% by wt, typically more than 80% by wt of olefins, the remainder being mostly cycloolefins, olefins, unreacted ethylene, paraffins and cycloparaffins, and less than 2% by wt aromatics.

It is therefore a general object to provide a process for oligomerizing an olefin-containing feedstream consisting essentially of "light gas" containing predominantly $C_3=+$ olefins, to distillate ($C_9+$ hydrocarbons), comprising, operating a dense phase fluid-bed in the turbulent regime at moderate pressure and moderate temperature conditions while flowing the light gas feed through the bed which consists essentially of a finely divided medium pore zeolite metallosilicate catalyst having a constraint index in the range from 1 to 12 and consisting essentially of specified weight fractions of equilibrated low activity catalyst particles, each weight fraction having an alpha in a preselected range from about 1 to below 10, these weight fractions totalling at least 90% by wt, the remaining weight fractions totalling less than 10% by wt of the catalyst having an alpha greater than 10; and, to provide a low severity MOD reactor which in combination with a regenerator, is particularly adapted to carry out the foregoing process.

It is a specific object to provide a process for the continuous conversion of a lower olefin feedstock gas to distillate, in which process the feedstock is contacted with a fluidized bed of zeolite catalyst under conversion conditions, the process comprising, equilibrating the fluid bed of catalyst which consists essentially of finely divided medium pore zeolite metallosilicate particles having a constraint index in the range from 1 to 12, the bed having an average activity (alpha) in the range from 2 to about 10 and consisting essentially of preselected weight fractions of low activity catalyst particles totalling at least 90% by wt having an alpha no greater than 10, the remaining less than 10% by wt of the catalyst particles having an alpha greater than 10;

passing said feedstock gas in the substantial absence of added propane upwardly through the fluidized bed in a vertical reactor column having a turbulent reaction zone, while maintaining a superficial velocity in the range from 0.3 to 2 m/sec so that catalyst particles in which the silica:alumina molar ratio is in the range from about 20:1 to about 200:1 are held in a turbulent regime;

maintaining an average density, measured at the bottom of the fluidized bed in the range from about 264 to 608 kg/m$^3$, at a pressure in the range from 200 kPa to 2800 kPa and a temperature in the range from about 250° C. to about 371° C.;

withdrawing a portion of coked catalyst from the reaction zone, oxidatively regenerating the withdrawn catalyst and returning regenerated catalyst to the fluidized bed at a rate sufficient to maintain a reaction severity index, expressed as the propane:propene weight ratio in the hydrocarbon product, in the range from about 0.2:1 to 5:1, whereby at least 10% by wt, and preferably more than 20% by wt of said feedstock is converted to a substantially olefinic $C_9=+$ distillate.

It is a specific object of this invention to provide an economical process for directly converting lower olefins into distillate in a single pass through a turbulent fluid bed, with the amount of distillate produced ranging from about 20% to 50% by wt of the $C_5$ product, the remaining product being $C_9-$ gasoline range hydrocarbons. The remaining $C_9-$ gasoline range olefins, typically not desired in our process, include tertiary olefins. The undesired $C_9-$ olefins are separated for further use. They may be (i) blended into gasoline, (ii) recycled to the MOD reactor to produced additional distillate, or (iii) reactive tertiary olefins may be converted into ethers, and (iv) lower and intermediate olefins may be reacted at high pressure and moderate temperature to form $C_{10}+$ aliphatics.

BRIEF DESCRIPTION OF THE DRAWING

The foregoing and other objects and advantages of our invention will appear more fully from the following description, made in connection with the accompanying drawings of a preferred embodiment of the invention, wherein.

DETAILED DESCRIPTION OF PREFERRED EMBODIMENTS

The process of this invention is specifically directed to producing an essentially olefinic distillate from a predominantly olefinic light gas feedstock under moderate severity and relatively low pressure conditions. The process is carried out in a fluidbed of catalyst under process conditions at which the fluidizing medium is never at, or below its dewpoint. Therefore, if operation at a pressure at the top of the range is sought, the temperature at which the fluid-bed operates is raised so that the mixture of hydrocarbons in the fluid-bed is above its dew-point.

In the preferred embodiment, the process of this invention uses an olefinic light gas feedstock (commonly referred to as olefinic LPG) having the following composition:

$C_3=$: 25.5% by wt.
$C_3$: 7.6%
$C_4$: 43.7%
$C_4$: 25.14%

In operation with the preferred feed, a typical operating pressure is about 445 kPa (50 psig), and temperature is about 316° C. (600° F.), though the reactor may be operated at as low a superatmospheric pressure as 200 kPa (15 psig).

Figure 1:
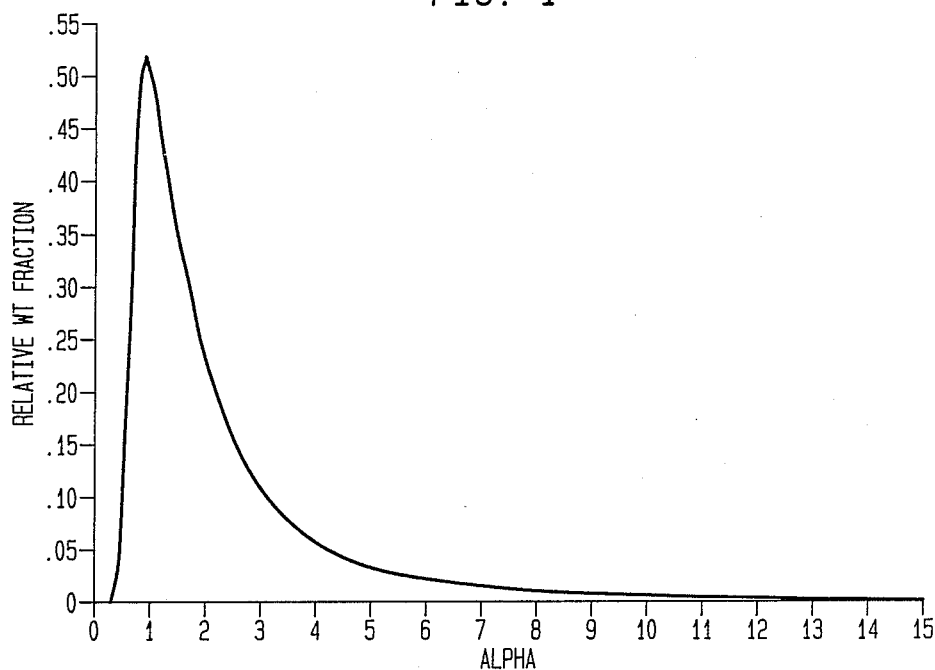
FIG. 1 is a curve graphically illustrating a typical distribution of activity (alpha) as a function of the relative weight fraction of catalyst particles in the fluid bed of the reaction vessel.

Referring to FIG. 1 there is shown a representative curve of a fluid bed of equilibrated catalyst referred to as "3-alpha catalyst" because it is the preferred average alpha for the fluid-bed less than 10% by wt of the fluid-bed has an equilibrated alpha greater than about 5. The particular preferred ZSM-5 type catalyst chosen for the fluid bed is less critical than the low average alpha, which in turn is less critical than the general distribution of alphas for relative weight fractions of catalyst in the bed. In other words, a preferred bed has an average alpha in the range from about 2 to about 10, but it is essential that preselected weight fractions totalling about 90% have an alpha no greater than 10, the remaining having an alpha greater than 10.

A preferred fluid-bed for which the curve is shown in FIG. 1 has a distribution of the following alphas for the weight fractions specified:

| Rel. wt. frac. | alpha |
|---|---|
| 0.50 | <1 |
| 0.25 | 2 |
| 0.10 | 3 |
| 0.05 | 4 |
| remainder | >5 |

The precise weight fraction having the foregoing approximate alphas is not narrowly critical provided the weight fractions having specified alphas lie in the following ranges:

| Range of rel. wt. frac. | alpha |
|---|---|
| 0.20 to 0.60 | <1 |
| 0.15 to 0.35 | 1 to 3 |
| 0.05 to 0.20 | 3 to 5 |
| 0.03 to 0.20 | 5 to 10 |
| remainder | >5 |

Figure 2:
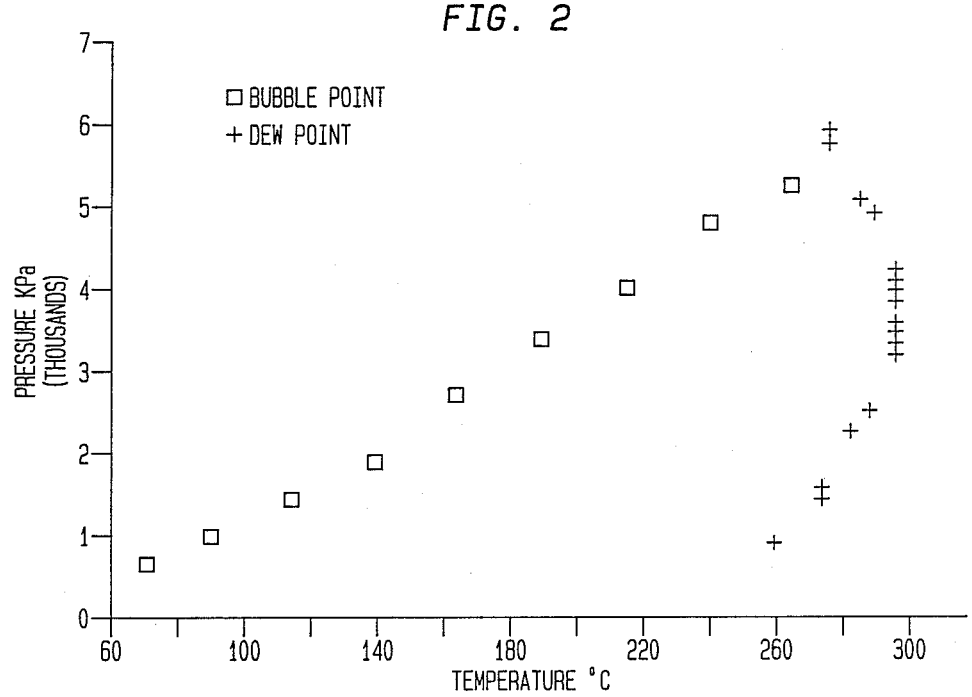
FIG. 2 is a phase diagram showing a plot of dew-point and bubble-point curves for a representative distillate produced in our process.

Referring to FIG. 2, the phase diagram shown is for a most desirable distillate identified by its components listed herebelow, over a range of temperature and pressure ranging from about 65.5° C. (150° F.) and about 1240 kPa (180 psia), to the critical point, which is at about 282° C. (540° F.) and 5994 kPa (870 psia).

$C_2^=$: 0.03% by wt.
$C_3^=$: 0.09%
$C_3$: 7.6%
$C^=$: 1.19%
$C_4$: 23.14 %
$C_5-C_9$: 28.96%
$C_{10}^+$: 38.99%

Oligomerization of the feed can be effected in a single zone, that is, a single fluid bed operating in the dense phase because the heat duty of the reaction exotherm is transferred to cooling fluid flowing through coils in the reactor. The use of prior art multiple fixed beds in each of which only about a 28° C. (82° F.) exotherm may be accomodated, is avoided. The operating conditions for the fluid bed reactor to produce the foregoing product is as follows:

Temperature (inlet): 300° C. (572° F.)
WHSV: 0.3 hr$^{-1}$
Pressure (inlet): 480 kPa (55 psig)

There is no hydrogen introduced to the reactor, and no liquid recycle. It will be understood that the inlet temperature is typically lower than the bed temperature because the reaction exotherm raises the temperature, and heat transfer to the cooling coils in the bed is controlled to maintain the desired bed temperature.

The turbulent fluidization regime in our process is characteristic of a conventional dense phase turbulent fluid bed operating at a pressure below 2857 kPa (400 psig), and readily distinguishable from non-turbulent dense beds and transport beds. The bed density of our dense phase bed does not exceed 640 kg/m$^3$ (40 lb/ft$^3$), generally being in the range from about 264 kg/m$^3$ (16.5 lb/ft$^3$) to about 448 kg/m$^3$ (28. lb/ft$^3$).

The bed density is correlatable with operating pressure of the bed at a specified superficial velocity, as follows:

| Pressure | Bed dens., @ 0.3 m/sec | Bed dens., @ 0.61 m/sec |
|---|---|---|
| kPa (psig) | kg/m$^3$ (ft$^3$/sec) | kg/m$^3$ (ft$^3$/sec) |
| 273 (25) | 608 (38) | 400 (25) |
| 1480 (200) | 448 (28) | 295 (18.5) |
| 2857 (400) | 400 (25) | 264 (16.5) |

The preferred particle density is preferably in the range from about 1.2–2.5 g/cc. A typical dense fluid bed has a minimum fluidization velocity of 0.014 m/sec (0.047 ft/sec) and operates at a superficial velocity in the range from about 0.3–2.0 m/sec (1–6.5 ft/sec).

A distillate with a comparable distribution of olefins may be produced from the same light gas feed using a low alpha catalyst in multiple fixed bed reactors, but only if they are operated under higher severity and higher conditions of temperature, pressure, and residence time as those in the ranges specified for our dense bed. Three fixed bed reactors in series are used as described in the prior art, with progressively diminishing inlet temperatures of 254.4° C. (490° F.); 248.9° C. (480° F.); and 243.3° C. (470° F.). The first reactor inlet pressure is 6787 kPa (985 psia) and a H$_2$ circulation rate of 250 SCF/BBL and diluent rate=105,000 lb/hr. The hydrogen is essential to keep coke deposition on the catalyst to an acceptable level and also as a preventitive measure against poisoning of the catalyst by nitrogen-containing organic compounds. The analysis for product from the multiple fixed beds is as follows:

$C_2^=$: 0.14% by wt.
$C_3^=$: 8.4
$C_3$: 2.3
$C_4^=$: 21.14
$C_4$: 5.14
$C_5-C_9$: 28.28
$C_{10}^+$: 32.65

When the operation of the three fixed beds is changed to match generally the pressure and temperature conditions of our low severity fluid bed process, the following conditions prevail in each of the fixed beds:

| | Pressure | Temperature | |
|---|---|---|---|
| | kPa (psig) | °C. (°F.) | WHSV, hr$^{-1}$ |
| First | 380 (55) | 316 (600) | 0.5 |
| Second | 345 (50) | 310 (590) | 0.5 |
| Third | 310 (450) | 304 (580) | 0.5 |

The analysis of product from the multiple fixed beds operated with recycle to maximize $C_5^+$"make" under the foregoing low severity conditions is as follows:

$C_2^=$: 0.0% by wt.
$C_3^=$: 7.1
$C_3$: 1.0
$C_4^=$: 26.7
$C_4$: 1.2
$C_5-C_9$=62.5

$C_{10}=+$: 1.5

Figure 3:
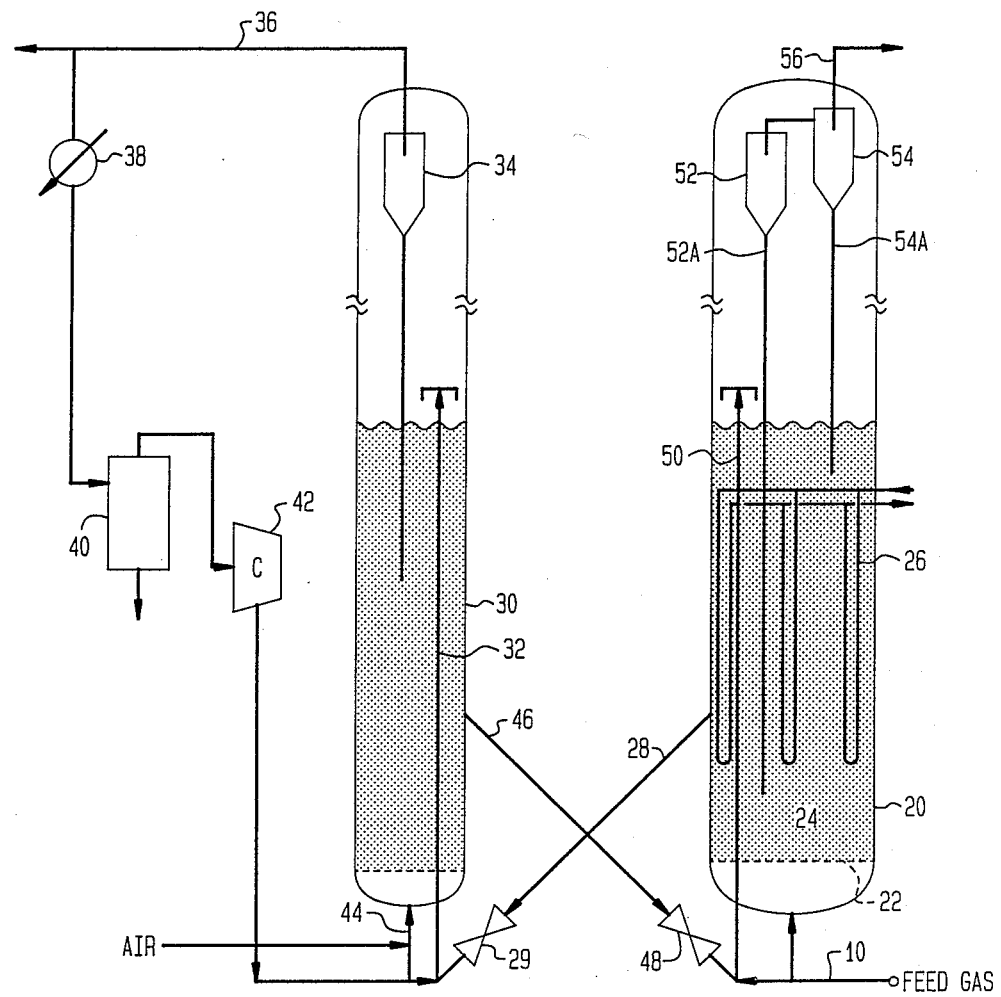
FIG. 3 is a flowsheet schematically illustrating the use of a relatively low pressure fluid bed reactor in association with a regenerator in which coked up catalyst is oxidatively regenerated and returned to the reactor, either periodically, or continuously.

Referring now to FIG. 3, a light-gas feed rich in $C_3$–$C_4$ olefins passes, through conduit 10, into the reaction vessel 20, with the main flow being directed through the bottom inlet for distribution through grid plate 22 into the fluidization zone 24. Here the gaseous feed contacts the turbulent bed of finely divided catalyst particles. Reaction vessel 20 is shown provided with heat exchange tubes 26, which may be arranged as several separate heat exchange tube bundles so that temperature control can be separately exercised over different portions of the fluid catalyst bed. The bottoms of the tubes are spaced above feed distributor grid 22 sufficiently to be free of jet action by the charged feed through the small diameter holes in the grid. Alternatively, a substantial portion of the reaction heat can be removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction may also be controlled by adjusting feed temperature in a known manner.

Catalyst outlet means 28 is provided for withdrawing catalyst from above bed 24 and passed for catalyst regeneration in vessel 30 via control valve 29. The partially deactivated catalyst is preferably stripped with an inert gas (steam or nitrogen) in a stripper (not shown), and oxidatively regenerated by controlled contact with air or other regeneration gas at an elevated temperature in a fluidized regeneration zone to remove carbonaceous deposits and restore acid activity. The catalyst particles are entrained in a lift gas and transported via riser tube 32 to a top portion of vessel 30. Air is distributed at the bottom of the bed to effect fluidization, with oxidation byproducts being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40, and compressor 42 for return to the vessel with fresh oxidation gas via line 44 and as lift gas for the catalyst in riser 32.

Regenerated catalyst is passed to the reaction vessel 20 through conduit 46 provided with flow control valve 48. The regenerated catalyst may be lifted to the catalyst bed with pressurized feed gas, through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separators 52, 54 are provided with diplegs 52A, 54A to return any entrained catalyst fines to the lower bed. These separators are positioned in an upper portion of the reactor vessel containing dispersed catalyst phase 24. Filters, such as sintered metal plate filters, can be used alone or in conjunction with cyclones.

The product effluent, separated from catalyst particles in the cyclone separating system, is then withdrawn from the reactor vessel 20 through top gas outlet means 56. The recovered hydrocarbon product comprising mainly $C_5$+ olefins with less than 20 % by wt aromatics, paraffins and naphthenes is thereafter processed a required, to provide the desired distillate.

By virtue of the turbulence experienced in the turbulent regime, gas-solid contact in the catalytic reactor is improved, providing at least 80% conversion of $C_3$–$C_6$ alkenes, enhanced selectivity, and temperature uniformity. Because of the relatively low pressure, bubbles of the gaseous reaction mixture are relatively large, and relatively long-lived, which would normally result in such poor contact between the gaseous reactants and the solid catalyst particles that typically, only a minor amount by weight of the olefins would be oligomerized. But the effect of the tailored activity of the catalyst particles is such that at least 75% of propylene and heavier olefins ($C_3$=+) and in the most preferred operation, more than 95% of the butenes and about 99% of the propene is converted.

Under optimized process conditions, the turbulent bed has a superficial vapor velocity of about 0.1 to about 1 m/sec (0.328 to 3.28 ft/sec). At higher velocities, entrainment of fine particles may become excessive and beyond about 2 m/sec (6.5 ft/sec) the entire bed may be transported out of the reaction zone.

A preferred, typical dense turbulent bed, has an operating density of about 600 kg/m$^3$ (38 lb/ft$^3$) to 300 kg/m$^3$ (18.5 lb/ft$^3$), measured at the bottom of the reaction zone, becoming slightly less dense toward the top of the reaction zone, due to pressure drop and particle size differentiation. Pressure differential between two vertically spaced points in the reactor volume may be measured to obtain the average bed density at such portion of the reaction zone. For instance, in a fluidized bed system employing HZSM-5 particles having an apparent packed density of 750 kg/m$^3$ and real density of 2430 kg/m$^3$, an average fluidized bed density of about 500 to 600 kg/m$^3$ is satisfactory.

The MOD reactor is operable with shape selective medium pore catalysts exemplified by ZSM-5, ZSM-11, ZSM-12, ZSM-23, ZSM-35, ZSM-38, ZSM-48 and other similar materials. U.S. Pat. No. 3,702,886 describing and claiming ZSM-5; U.S. Pat. No. Re. 29,948 describing and claiming a crystalline material with an X-ray diffraction pattern of ZSM-5; and, U.S. Pat. No. 4,061,724 describing a high silica ZSM-5 referred to as "silicalite" are each incorporated by reference thereto as if fully set forth herein. Similarly, the disclosures relating to ZSM-11, ZSM12, ZSM-23, ZSM-35, ZSM-38, and ZSM-48 set forth in U.S. Pat. Nos. 3,709,979, 3,832,449, 4,076,842, 4,016,245, 4,046,859, and 4,375,573, respectively, are each incorporated by reference thereto as if fully set forth herein.

In general the aluminosilicate zeolites are most effectively employed in our MOD reactor. However, zeolites in which some other framework element which is isoelectronic to aluminum and which is present in partial or total substitution of aluminum can be advantageous. Illustrative of elements which can be substituted for part or all of the framework aluminum are boron, gallium, titanium, and, in general, any trivalent metal which is heavier than aluminum. Specific examples of such catalysts include ZSM-5 and zeolite Beta containing boron, gallium and/or titanium. In lieu of, or in addition to, being incorporated into the zeolite framework, these and other catalytically active elements can also be deposited upon the zeolite by any suitable procedure, e.g., by impregnation.

The aluminosilicates are preferred catalysts. These can be described as a three-dimensional framework of $SiO_4$ and $AlO_4$ tetrahedra in which the tetrahedra are cross-linked by the sharing of oxygen atoms whereby the ratio of total aluminum and silicon atoms to oxygen atoms is 1:2. In their hydrated form, the aluminosilicates may be represented by the formula:

$$M_{2/n}O:Al_2O_3:wSiO_2:YH_2O$$

wherein M represents at least one cation which balances the electrovalence of the tetrahedra, n represents the valence of the cation, w the moles of $SiO_2O$ and Y the moles of $H_2$. The cations can be any or more of a number of metal ions, depending upon whether the aluminosilicate is synthesized or occurs naturally. Typical cations include sodium, lithium, potassium, silver, magnesium, calcium, zinc, barium, iron, nickel, cobalt and manganese. Although the proportions of inorganic oxides in the silicates and their spatial arrangements may vary affecting distinct properties in the aluminosilicate, the main characteristic of these materials is their ability to undergo dehydration without substantially affecting the $SiO_4$ and $AlO_4$ framework.

Aluminosilicates falling within the above formula are well known and, as noted, include synthesized aluminosilicates, natural aluminosilicates, and certain caustic treated clays. Among the aluminosilicates are included zeolites, Y, L, S, X, levynite, erionite, faujasite, analcite, paulingite, noselite, phillipsite, datolite, gmelinite, leucite, scapolite, mordenite as well as certain caustic treated clays such as montmorillonite and kaolin families. The preferred aluminosilicates are those having pore diameters of greater than about 6 Å (Angstroms).

Aluminosilicates may be treated with a fluid medium or media in a known manner to include a wide variety of aluminosilicates both natural and synthetic which have a crystalline, or, combination of crystalline and amorphous structure. These "promoters" may be provided in the catalyst by impregnation or ion exchange.

Though the process of the invention is operable with any of the aluminosilicates the preferred catalyst is a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 type structures may be utilized by employing highly siliceous materials or crystalline metallosilicate having one or more tetrahedral species having varying degrees of acidity. The ZSM-5 crystalline structure is readily recognized by its X-ray diffraction pattern, which is described in U.S. Pat. No. 3,702,866 (Argauer, et al.), incorporated by reference herein.

The oligomerization catalysts preferred for use herein include the medium pore (i.e., about 5–7Å) shape-selective crystalline aluminosilicate zeolites having a silica-to-alumina ratio of at least 12, a constraint index of about 1 to 12, acid cracking activity of about 10–250, and, in the MOD reactor, it is essential that the coked catalyst have the tailored equilibrated activity referred to hereinabove to achieve the required selectivity and per pass conversion. Representative of the ZSM-5 type zeolites are ZSM-5, ZSM-11, ZSM-12, ZSM-22, ZSM-23, ZSM-35 and ZSM-38. Details about ZSM-5 are disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,046,839; 4,414,423; 4,417,086; 4,517,396 and 4,542,251, the disclosures of which are incorporated by reference thereto as if fully set forth herein. A typical zeolite catalyst component having Bronsted acid sites may consist essentially of aluminosilicate ZSM-5 zeolite with 5 to 95 wt % silica and/or alumina binder.

These siliceous zeolites may be employed in their acid forms, ion exchanged, or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g. ionic $Ni^{+2}$, and a shape-selective medium pore acidic oligomerization catalyst, such as ZSM-5 zeolite) which components may be present in admixture or combined in a unitary bifunctional solid particle.

Certain of the ZSM-5 type medium pore shape selective catalysts are sometimes known as penfasils. In addition to the preferred aluminosilicates, the borosilicate, ferrosilicate and "silicalite" materials may be employed. It is advantageous to employ a standard ZSM-5, suitably modified, having a silica:alumina molar ratio in the range from 12:1 to 100:1, a constraint index in the range from 5 to 12, and with the aforesaid average alpha to convert substantially all the olefins in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02–1 micron being preferred, and an apparent crystal density in the range from about 0.6 to 1.9 $gm/cm^3$. In order to obtain the desired particle size for fluidization in the turbulent regime, the zeolite catalyst crystals are bound with a suitable inorganic oxide, such as silica, alumina, etc. to provide a zeolite concentration of about 5 to 95 wt %. In the best mode a bed of 25% HZSM-5 catalyst contained within a silica-alumina matrix and having the aforementioned distribution of equilibrated alpha, is employed.

Operation of a dense phase turbulent regime with the preferred catalyst is distinguished by its particle size distribution to achieve overall homogeneity, particularly requiring from about 10% to 20% of "fines". It is advantageous to employ a particle size range consisting essentially of 1 to 200 microns. Average particle size is usually about 20 to 150 microns, preferably 50 to 100 microns. The optimum particle size distribution is obtained with a mixture of larger and smaller particles within the above-specified range, having from 15–20% by weight fines. Close control of distribution is maintained with the fines in the size range less than 32 microns.

The average particle density of the catalyst as used may be tailored for optimum fluid-bed operation by compositing it with a matrix component of appropriate density. Such matrix components which provide particles of progressively increasing overall packed density are silica, alumina, beryllia, magnesia, barium oxide, zirconia, and titania, yielding values of from about 2.2 gm/cm$^3$ for silica, up to about 5.9 gm/cm$^3$ for zirconia. In our MOD reactor, the overall packed density of medium pore zeolite particles so composited, including the matrix component, can advantageously vary from about 0.6 to about 4 gm/cm$^3$, more preferably from about 2 to about 3 gm/cm$^3$.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. When these solid particles are placed in a fluidized bed where the superficial fluid velocity is 0.06-0.5 m/s, operation in the turbulent regime is obtained. Those skilled in the art will appreciate that at higher pressures in the range, a lower gas velocity may be employed to ensure operation in the turbulent fluidization regime.

The MOD reactor is designed as a moderate pressure vessel required to contain a turbulent fluid-bed operating to produce optimum yields of the desired oligomers, and important criteria are taken into consideration. The bed of catalyst in the reactor is desirably in the range from about 3-20 meters in height, preferably about 8 meters, and, operates at relatively low WHSV, most preferably less than 1 hr$^{-1}$. Fine particles are deliberately included in the bed, some of which are due to attrition, and the fines may be entrained in the product gas stream. A typical turbulent bed may have a catalyst carryover rate of about 1.5 times the reaction zone inventory per hour. If the fraction of fines becomes large, a portion of the carryover may be removed from the system and replaced by larger particles. It is desirable to have a fine particle separator such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a sintered metal filter operating at the MOD reactor conditions.

Typically, in carrying out the process in the relatively low pressure MOD reactor, the light gas feed is brought into contact with a medium pore zeolite catalyst having a silica to alumina ratio in the range from 12 to about 1000, more preferably from 50 to 90, maintained as a dense phase in a fluid-bed at about 274 kPa to 1480 kPa (25 psig-200 psig), at a temperature below 371° C. (700° C.) at which conditions no liquid will form in the bed, while the light gas is flowed through the reactor at a superficial vapor velocity preferably in the range from about 0.15 m/sec (0.5 ft/sec) to about 0.305 m/sec (1 ft/sec) over a HZSM-5 catalyst having a constraint index in the range from 5-12, and, an equilibrated alpha in conformance with the curve shown in FIG. 1, and operating with a WHSV (based on olefin equivalent and total reactor catalyst inventory) in the range from about 0.1 to 1 hr$^{-1}$.

The operation of the turbulent fluid bed in the dense phase produces a remarkably low coking rate, less than 0.3 wt %, and preferably less than 0.05 wt % of the olefins in the feed, which low rate allows one to operate the bed without regeneration for a long period of time. In some instances periodic regeneration may be a preferred mode of operation. If not continuously regenerated, the coke content will gradually increase to about 15% by wt of the catalyst, at which point the run is desirably terminated.

When continuous regeneration is chosen, the regenerator will be operated at the lowest pressure at which effective decoking can be quickly effected without exceeding a temperature deleterious to the activity of the regenerated catalyst. Typically, the regeneration pressure is in the same range as that for the reactor. Whether withdrawal of coked-up catalyst is periodic or continuous, the desired activity of the regenerated catalyst is maintained such that the equilibrated activity of the fluid-bed during operation of the reactor will be generally in conformance with the curve shown in FIG. 1.

Equilibrating the activity of the specified weight fractions of the fluid-bed catalyst, rather than providing a generally uniform fluid-bed with the desired average alpha, is the distinguishing characteristic of our process. The unique effect of this tailored equilibrated activity is evidenced by (i) a per pass conversion of lower olefins of at least 80%, typically better than 90%, and a selectivity to $C_5^+$ hydrocarbons typically exceeding 80%; and (ii) formation of less than 5% by wt of aromatics. Because $C_9^-$ hydrocarbons in the product are not particularly desirable, operating conditions are chosen so that a relatively very small amount of gasoline range hydrocarbons, less than about 20 % by wt of distillate, are made during operation. Typically, the ratio of distillate to gasoline range hydrocarbons is 5:1, and may be as much as 10:1.

Another distinguishing characteristic of our process is that lower $C_2$-$C_5$ alkanes in the feed, if present, are substantially unconverted; that is, there is no net depletion of alkanes in the product. This can be accounted for by the formation of some $C_2$-$C_5$ alkanes with a purely $C_3$-$C_5$ olefinic feed.

To maintain the high per pass conversion and selectivity in the dense bed, the catalyst is preferably continuously regenerated. Whether regeneration is periodic or continuous, it is done by withdrawing a portion of coked catalyst from the reaction zone, oxidatively regenerating the withdrawn catalyst and returning regenerated catalyst to the reaction zone at a rate sufficient to maintain the desired selectivity and per pass conversion, each at least 80%, based on the total olefins in the feedstream.

It will be appreciated that the design, construction and operating conditions of a commercial oligomerization reaction vessel will be dictated by the economics of producing distillate, and the optimum operating conditions will be dictated by the conversions sought. Such a reactor will have a height to diameter ratio of at least 5, a pressure rating of at least 2800 kPa, and a temperature rating of at least 380° C. The feed to the reactor will preferably be preheated by the internal coils 26 through which liquid feed is pumped under sufficient pressure to provide a gaseous feed to the fluid bed, and at a temperature not much lower than about 20° C. from the desired operating temperature in the fluid bed. The regenerator will typically operate in the range from about 371° C.-510° C. (700° F.-950° F.), and the flue gas from the regeneration zone will be cooled to a sufficiently low temperature in the range from about 35° C. −50° C.

(95° F. —122° F.), so that a portion of it may be recycled to the regeneration zone, and the remainder discharged.

In the best mode for the production of distillate range hydrocarbons from an essentially monoolefinic light gas feedstock having at least 75% by wt of $C_3$-$C_6$ alkenes, the oligomerized product will contain less than about 80% by wt of ($C_9^-$) hydrocarbons, and about 20% by wt, or more, of ($C_9^+$) hydrocarbons. In most instances, a major portion of the $C_9^-$ hydrocarbons are separated from the product stream and recycled to the dense reaction zone.

EXAMPLE

In this illustrative example, the process is carried out in a 4 BPSD (bbls/stream day) pilot plant in which a moderate pressure reactor is used. The reactor is provided with a bed of medium pore HZSM-5 zeolite catalyst having a silica to alumina ratio of about 0, and the usual means for controlling fluidization of the bed in the turbulent regime. The HZSM-5 catalyst has a constraint index of about 10. The activity of the bed is tailored so as to fall approximately along the curve shown in FIG. 1. The feedstream is essentially pure propylene which is brought into contact with the catalyst which is maintained as dense phase in a fluid-bed at a pressure of 445 kPa (50 psig) and, with the inlet temperature of the feed being 254.4° C. (490° F.), the temperature of the bed is maintained at 315.5° C. (600° F.). The light gas is flowed through the reactor at a WHSV of 0.36 hr$^{-1}$, operating in the distillate mode, and the results are for a single pass, that is, without any recycle of $C_5$-$C_9$ gasoline range hydrocarbons.

For comparison, the same feed is flowed through a series of fixed bed reactors operating under low severity conditions defined by substantially the same pressures and temperatures specified hereinabove for them, with the same flow of hydrogen and inert diluents, and recycle of lower olefins to maximize the production of $C_5$-$C_9^=$ components.

The analyses of products made in each of the runs are presented side-by-side in Table I below, as % by wt of the product:

TABLE I

|  | % by wt in the product | |
|---|---|---|
|  | Fluid Bed | Fixed Bed |
| $C_2^=$ | 0.2 | 0.0% by wt. |
| $C_3^=$ | 5.62 | 7.1 |
| $C_3$ | 0.38 | 1.0 |
| $C_4^=$ | 12.02 | 26.7 |
| $C_4$ | 1.96 | 1.2 |
| $C_5$-$C_9^=$ | 67.93 | 62.5 |
| $C_{10}^=+$ | 11.75 | 1.5 |

As is evident from the foregoing example, the per pass conversion is better than 80%. Typically, the per pass conversion is over 90%, though in some cases where the olefin content is relatively low, the per pass conversion may be less.

Having thus provided a general discussion, and a specific illustration of the best mode of operation of a single zone, dense, turbulent fluid bed operating at relatively low pressure and moderate temperature, and described the oligomerization of a predominantly monomeric olefinic light gas feedstream in such a bed, it is to be understood that no undue restrictions are to be imposed by reason thereof, except as provided by the following claims.

We claim:

1. A catalytic process for converting an essentially $C_3^+$ olefin feedstream to distillate in a fluid bed of catalyst, said process comprising,
   (a) equilibrating said fluid bed of catalyst which consists essentially of finely divided medium pore zeolite metallosilicate particles having a constraint index in the range from 1 to 12, said bed having an average activity, alpha, in the range from about 2 to 10, said bed consisting essentially of preselected weight fractions of low activity catalyst particles adding up to about 90% by weight having an alpha no greater than 10, the remaining less than 10% by weight having an alpha greater than 10;
   (b) contacting said olefin feedstream with said catalyst maintained as a dense fluid-bed operating in a single zone turbulent regime at superatmospheric pressure but below about 2800 kPa (400 psig) and a temperature above the dewpoint of the hydrocarbon mixture in the bed at operating pressure,
   (b) flowing said olefin feedstream through said bed at a weight hourly space velocity (WHSV) in the range from about 0.05 to about 5 hr$^{-1}$,
   (c) maintaining a catalyst fines content of from about 10% to about 25% by wt, based on the weight of the catalyst in the bed, said fines having a particle size less than 32 microns, and,
   (d) converting at least 80 % by wt of said feedstream to olefins in a product which is essentially free of aromatics, with a yield per pass of about 20 percent by weight of said distillate.

2. The process of claim 1 wherein said olefin feedstream is essentially monoolefinic consisting essentially of $C_3$-$C_6$ monoolefins, and, said average alpha of said fluid bed consists of relative weight fractions having the following alphas:

| Range of rel. wt. frac. | alpha |
|---|---|
| 0.20 to 0.60 | <1 |
| 0.15 to 0.35 | 1 to 3 |
| 0.05 to 0.20 | 3 to 5 |
| 0.03 to 0.20 | 5 to 10 |
| remainder | >5 |

3. The process of claim 2 wherein said catalyst has a silica:alumina ratio greater than 12, and said bed operates at a bed density, measured at the bottom of the reaction zone, no greater than 608 kg/m$^3$, a temperature in the range from about 250° C. (482° F.) to about 371° C. (700° F.), and a pressure in the range from above about 200 kPa (15 psig) but below 2857 kPa (400 psig).

4. The process of claim 3 wherein said catalyst is a siliceous metallosilicate acid zeolite having a ZSM-5-type structure, said average alpha is 3, there is less than 10% by weight (0.1 relative weight fraction) of catalyst having an equilibrated alpha above 10, and said silica:alumina ratio is in the range from about 2:1 to 70:1.

5. The process of claim 4 wherein said $C_3$-$C_6$ monoolefins comprise a major proportion by weight of propene and butenes.

6. The process of claim 4 wherein said fluid bed is maintained in a reactor operated at relatively low pressure in the range from about 274 kPa (25 psig) to about 1480 kPa (200 psig), and moderate temperature in the range from 204° C. to about 371° C. (400° F.–700° F.); and, said distillate has a boiling in the range from about 138° C. to about 349° C. (280° F. - 660° F.).

7. The process of claim 4 wherein said essentially monoolefinic feedstream is essentially free of hydrogen.

8. A process for oligomerizing a "light gas" feedstream containing $C_2$-$C_6$ lower olefins and a minor proportion by weight of diluent $C_2$-$C_6$ paraffins, to an essentially olefinic $C_=^9+$ distillate by contacting the feedstream with a fluidized bed of zeolite catalyst under conversion conditions, the process comprising:

(a) equilibrating the fluid bed of catalyst which consists essentially of a finely divided medium pore zeolite metallosilicate particles having a constraint index in the range from 1 to 12, the bed consisting essentially of preselected weight fractions of low activity catalyst particles adding up to at least 90 wt %, each such weight fraction having an alpha no greater than 10, the remaining 10 wt % or less of the catalyst particles having an alpha greater than 10;

passing said feedstream as gas upwardly through the fluidized bed in a vertical reactor column having a turbulent reaction zone, while maintaining a superficial velocity in the range from about 0.3 m/sec to about 2 m/sec so that catalyst particles in which the silica:alumina molar ratio is in the range from about 20:1 to about 200:1 are held in a turbulent regime;

maintaining an average density, measured at the bottom of the fluidized bed in the range from about 250 to 600 kg/m$^3$, at a pressure in the range from about 2850 kPa to 200 kPa and a temperature in the range from about 204° C. to 371° C.;

withdrawing a portion of coked catalyst from the reaction zone, oxidatively regenerating the withdrawn catalyst and returning regenerated catalyst to the fluidized bed at a rate sufficient to maintain a reaction severity index, expressed as the propane:propene weight ratio in the hydrocarbon product, in the range from about 0.2:1 to 5:1, whereby at least 10% by weight of said feedstream is converted to a substantially olefinic $C_9=+$ distillate.

9. The process of claim 8 wherein said olefinic content of said feedstream consists essentially of at least 75% by wt of propylene and heavier olefins ($C_3=+$), and said turbulent bed has a fluidized height of at least 3 meters.

10. The process of claim 8, including in addition, the steps of separating hydrocarbons having less than 9 carbon atoms ($C_9-$) from said distillate, and, recycling said ($C_9-$) hydrocarbons to said reactor.

11. A fluidized bed catalytic process for converting a light olefinic gas feedstock to a distillate-rich predominantly olefinic stream, in a low activity, 'low-alpha', fluid bed of catalyst, which bed operates at relatively low pressure and moderate temperature, comprising, feeding said gas feedstock comprising at least 50 mol % propylene and heavier olefins $C_3=+$, to a catalytic fluid bed reaction zone, maintaining said fluid bed in a turbulent regime wherein pressure is in the range above atmospheric but below 2850 kPa, and temperature in the range from about 250° C. to 371° C., said catalyst being a particulate zeolite having a silica:alumina molar ratio in the range from about 20:1 to about 200:1, an apparent particle density of about 0.9 to 1.6 g/cm$^3$, a size range of about 20 to 100 microns, and average catalyst particle size of about 20 to 100 microns containing about 15 to 25 weight percent of fine particles having a particle size of less than 32 microns;

passing said gas feedstock in the substantial absence of added propane upwardly through said fluid bed in a single pass under turbulent flow conditions which provide reaction severity conditions sufficient to convert at least about 70% of olefins in said feedstock;

maintaining turbulent conditions at a superficial feedstock velocity of about 0.3 to 2 meters per second through said bed having an average fluidized bed density, measured at the bottom of the reaction zone, in the range from about 200 to 400 kg/m$^3$; and recovering hydrocarbon product containing a major amount of $C_4=+$ hydrocarbons containing at least 10% by weight of distillate and a ratio of propane:propene in the range from above 0.01:1 but below 0.2:1.

12. In a continuous process for converting a light hydrocarbon feedstock to heavier hydrocarbon products wherein the feedstock is contacted with a fluidized bed of zeolite catalyst under relatively low pressure and moderate temperature conversion conditions, the improvement which comprises equilibrating said fluid bed of catalyst which consists essentially of finely divided medium pore zeolite metallosilicate particles having a constraint index in the range from 1 to 12, said bed having an average activity, alpha, in the range from about 2 to 10, said bed consisting essentially of preselected weight fractions of low activity catalyst particles adding up to about 90% by weight having an alpha no greater than 10, the remaining less than 10% by weight having an alpha greater than 10;

maintaining the fluidized catalyst bed having an average density measured at the bottom of the reaction zone in the range from about 200 to 400 kg/m$^3$ and a catalyst fines content of from about 10% to about 25% by wt, based on the weight of the catalyst in the bed, said fines having a particle size less than 32 microns, at a pressure in the range from 274 kPa to 2857 kPa and a temperature in the range from about 250° C. to 371° C., in a vertical reactor column having a turbulent reaction zone, by passing said gas feedstock comprising at least 50 mol % propylene and heavier olefins $C_3=+$, while maintaining a superficial velocity in the range from about 0.3 m/sec to about 2 m/sec; and withdrawing a portion of coked catalyst, in which the silica:alumina molar ratio is in the range from about 20:1 to about 200:1, from the reaction zone, oxidatevely regenerating the withdrawn catalyst and returning regenerated catalyst to the reaction zone at a rate sufficient to maintain a reaction severity index expressed as the propane:propene weight ratio in the hydrocarbon product at about 0.01:1 to 0.2:1 whereby at least 70% of olefins in said feedstock is converted.

* * * * *